United States Patent [19]

King

[11] Patent Number: 4,977,850
[45] Date of Patent: Dec. 18, 1990

[54] SIGNAL APPARATUS

[76] Inventor: Morris T. King, 530 Central Ct., Indianapolis, Ind. 46205

[21] Appl. No.: 445,528

[22] Filed: Dec. 4, 1989

[51] Int. Cl.$^5$ .......................... G01F 23/00; G10K 1/10
[52] U.S. Cl. ..................................... 116/109; 116/155; 116/167; 248/125
[58] Field of Search ....................... 116/109, 155, 167; 177/45, 46, 118, 245; 604/245; 248/122, 125

[56] References Cited

U.S. PATENT DOCUMENTS

| | | | |
|---|---|---|---|
| 44,447 | 9/1864 | O'Donnell | 248/125 |
| 531,557 | 12/1894 | Paetow | 116/109 |
| 954,423 | 4/1910 | Cramer | 116/227 |
| 1,289,618 | 12/1918 | Billings | 116/109 |
| 1,441,191 | 1/1923 | Weiss | 116/109 |
| 2,143,706 | 1/1939 | Mathey | 116/109 |
| 2,212,620 | 8/1940 | Scully et al. | 116/109 |
| 2,897,853 | 8/1959 | Anstine | 141/95 |
| 3,115,152 | 12/1963 | Goldberg et al. | 177/245 |
| 3,557,789 | 1/1971 | Poitras | 604/245 |
| 4,678,049 | 7/1987 | Gummere et al. | 177/229 |

Primary Examiner—William A. Cuchlinski, Jr.
Assistant Examiner—W. Morris Worth
Attorney, Agent, or Firm—John H. Calhoun, Jr.

[57] ABSTRACT

A signal apparatus comprising a post-mountable arm adapted at one end to be mounted on a vertical stand post and having provided at the other end thereof a bell adapted to be struck by a counter-weight mounted on one end of a balance beam when blood reaches a predetermined level in a blood collection bag hung from the other end of the balance beam which is mounted on the said post below the said arm, and a hook adapted to receive a second bag removably hung thereon.

1 Claim, 2 Drawing Sheets

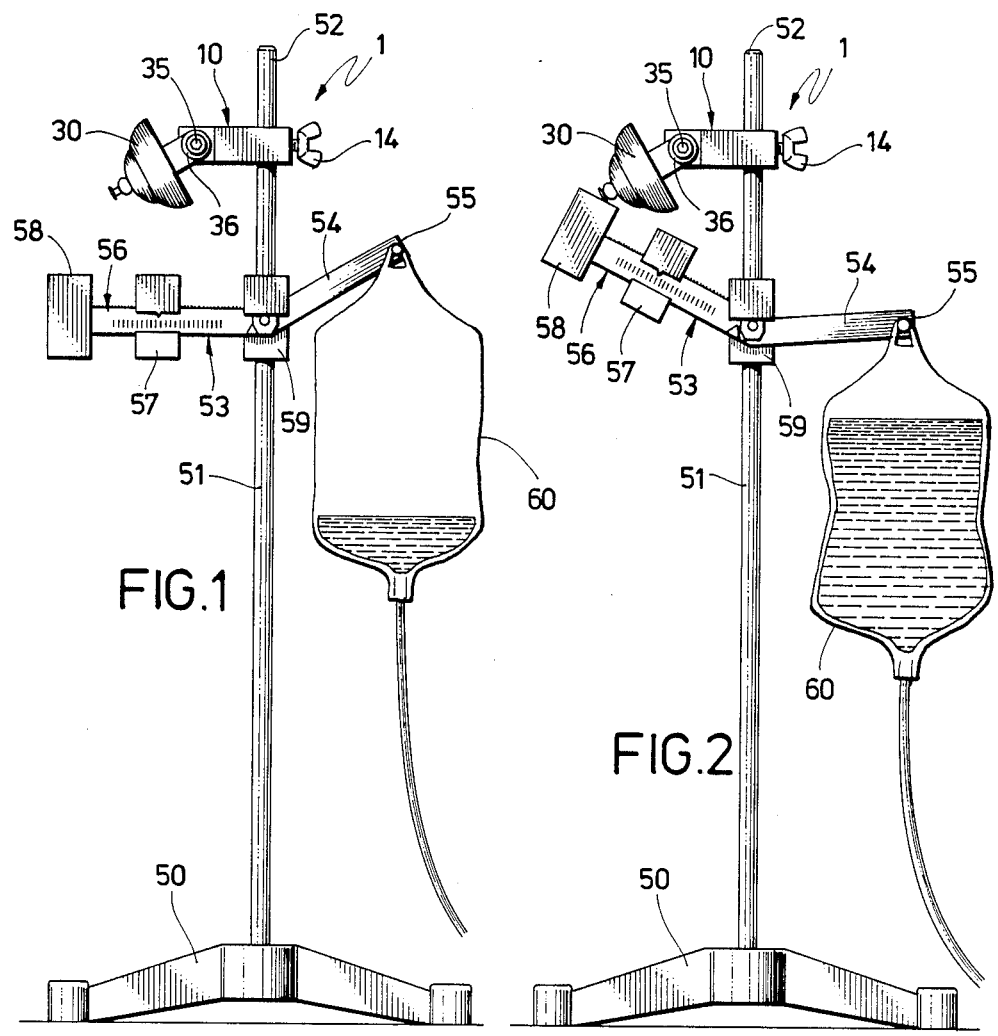
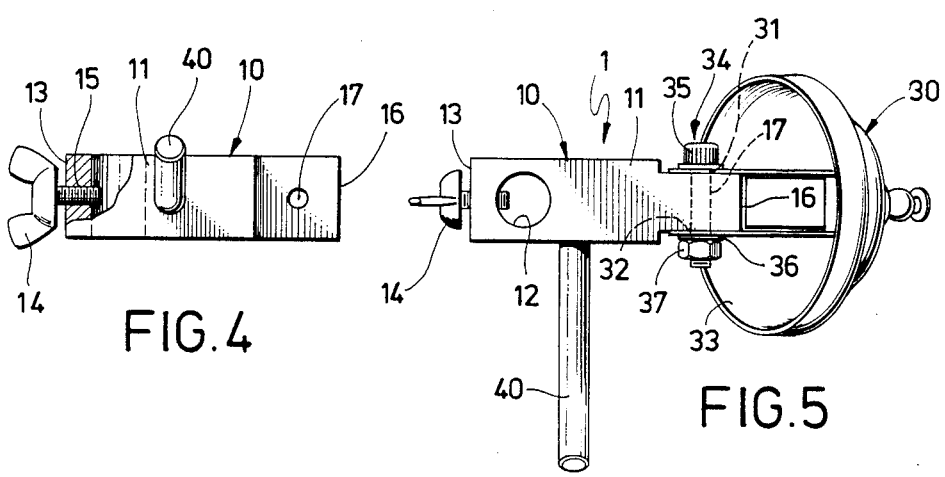

SIGNAL APPARATUS

BACKGROUND OF THE INVENTION

The present invention relates to an improved signal apparatus, that is a device that is used to alert a person to the happening of some particular event. The signal device of the present invention is based on the balance beam concept and is intended to provide a signal when a bag used to collect blood at a blood bank is full and needs to be disconnected from a donor. In the illustrated embodiment, an audible signal is given by a bell that is actuated by the movement of a counter-weighted arm when the bag at one end of the arm is full.

Signal devices of various kinds are well known in the prior art, as illustrated by U. S. Pat. No. 2,143,706 issued to 14 Alcide E. Mathey on Jan. 10, 1939 which shows a device that provides an audible signal to an operator when liquid in a tank reaches a predetermined level. U. S. Pat. No. 2,897,853 which issued on August 4, 1959 to Roland W. Anstine shows a filling indicator assembly for use with underground tank installations to indicate the level of liquid to which tanks are being filled. U. S. Pat. No. 2,212,620 which issued on Aug. 27, 1940 to Frank P. Sculley, et al. shows another device for indicating to an operator by audible signal means that the level of liquid in a tank has reached a predetermined level, so that the supply of liquid into the tank can be cut off in time to prevent overflow. U. S. Pat. No. 531,557 which issued on Dec. 25, 1894 to Eugen C. Paetow shows an alarm that is actuated when a certain level of liquid is collected in a pan. U.S. Pat. No. 954,423 which issued to Ernest A. Cramer on April 12, 1910 shows a fluid level indicator for use with lamps, and U.S. Pat. No. 1,441,191 which issued on Jan. 2, 1923 to Benjamin Weiss shows an improvement to signaling devices which provides for an alarm to be sounded repeatedly at intervals.

The present invention provides a novel and useful alarm apparatus that is uniquely adapted for use in the drawing of blood at blood banks

SUMMARY OF THE INVENTION

Blood banks collect blood in plastic bags by allowing blood to flow from a donor through a tube into a bag. A common practice is to place a bag at one end of a counter-weighted beam that is pivotally mounted on a stand post. When the collection bag is empty or only partially filled, it is held in a raised position by means of the counterweight at the other end of the beam. When the blood in the bag reaches a predetermined level, the weight of the blood filled bag overcomes the counterweight, causing the bag to drop into as lower position and the counterweight on the other end of the beam to raise to a higher position, in a teeter-totter like action.

The only way that a person in charge of drawing blood can know that a bag is full is for the person to constantly look at the bag as the blood level nears the top of the bag. It often happens that the person in charge is busy collecting blood from other donors of performing other tasks that make it difficult at best for the person in charge to constantly observe a particular bag. As a consequence, there is a substantial risk that too much blood may be drawn in a particular case.

Another common practice at blood banks is for the person in charge of drawing blood to maintain a second empty bag (later used when separating blood into its component parts) near the stand post so that when first bag is full the two bags may be promptly sent to a laboratory for processing of the blood.

A primary objective of the present invention is to provide an alarm apparatus that can be easily used with stand posts and counter-weighted beams commonly used by blood banks.

Another object of the present invention is to provide an audible signal which may be easily heard by a person in charge of drawing blood so that the person in charge may shut off the tube and thus avoid overflow.

Another object of the present invention is to provide an apparatus that makes use of bells of a kind that is commonly available.

Another objective of the present invention is to provide an apparatus that provides for storage of a second bag for convenience in processing blood.

Another object of the present invention is to provide a signal apparatus that is simple in construction, inexpensive, strong and durable, and well adapted for the purposes for which it is designed.

Other objects and advantages of the present invention will become apparent from a consideration of the following detailed description taken in connection with the accompanying drawings wherein a preferred embodiment of the invention are shown.

It should be understood that the invention is not limited to the details disclosed, but includes all such variations and modifications as fall within the spirit of the invention and the scope of the appended claims.

This invention contemplates signals other than audible signals may be employed within the scope of the present invention.

The objectives of the present invention are accomplished by providing a post-mountable arm that is adapted at one end for the installation of a bell and that is provided with a hook adapted to receive a spare bag removably hung thereon.

In the preferred embodiment illustrated herein the arm comprises a rectangular member having a first hole therethrough near a first end of the arm. The size and shape of the first hole are determined so that a stand post may be inserted through the first hole, and in the illustrated embodiment the first hole is round and is very slightly larger in diameter than the diameter of a commonly used stand post. The arm may be mounted onto a stand post by merely inserting an end of the post into the first hole and sliding the arm along the post to the desired position on the post. The arm may be securely fastened to the post to prevent further movement of the arm relative to the post by tightening a setscrew that may be operated through a threaded second hole at the first end of the arm.

The opposite or second end of the arm is adapted to receive a bell removably attached thereto. In the illustrated embodiment, the thickness of the arm is reduced at the second end of the arm to accommodate the installation of a bell that is commonly available. A third hole is provided through the second end of the arm. The size and location of the third hole are determined so that the third hole may be aligned with holes in a clamp that is commonly provided on the back of commercially available bells. Also, provided is a means for fastening the bell to the arm, which means comprises a suitably sized bolt, washer and nut.

Extending outward from and perpendicular to the arm is horizontal hook adapted to receive a spare bag removably hung thereon.

BRIEF DESCRIPTION OF THE DRAWINGS

A preferred embodiment of the present invention is illustrated in the accompanying drawings in which:

FIG. 1 is a front elevation view of the signal apparatus of the present invention which is mounted on a stand post and with an unfilled blood collection bag;

FIG. 2 is a front view of the signal apparatus of the present invention which is mounted on a stand post and with a filled blood collection bag;

FIG. 4 is a front cutaway view of the arm of the present invention;

FIG. 5 is top plan view of the arm of the present invention.

DESCRIPTION OF THE PREFERRED EMBODIMENT

Figure 3:
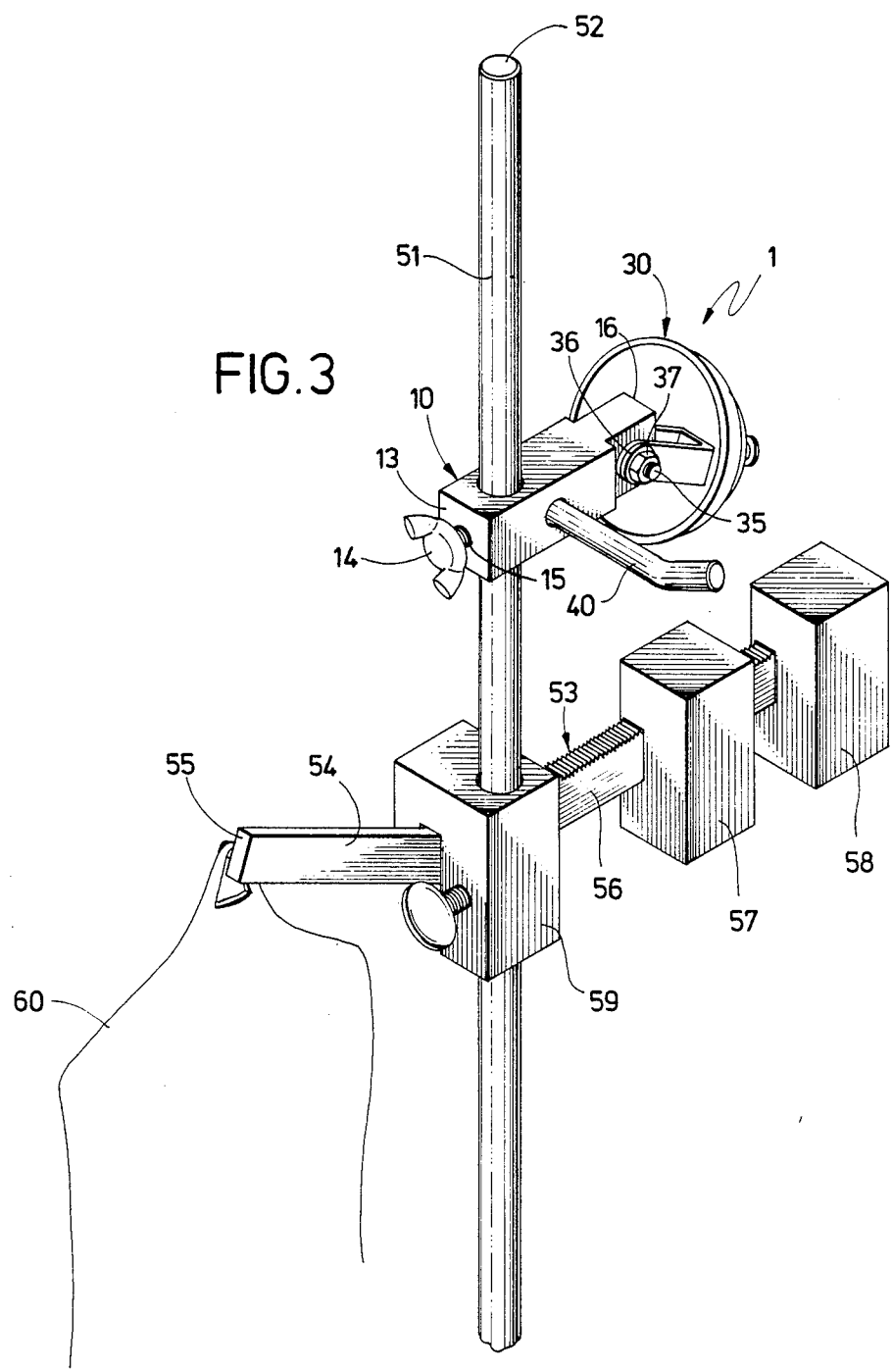
FIG. 3 is a view in perspective from the back of the signal apparatus which is mounted on a stand post.

Referring now to the drawings in greater detail, FIG. 1 illustrates the signal apparatus of the present invention, shown generally at 1, and mounted on a stand post 51 that is supported in a vertical position by a suitably designed base 50. Mounted by suitable means on the stand post 51 is balance beam 53 having a first arm 54 with an unfilled blood collection bag 60 hung from the free end 55 thereof and a second arm 56 having a pair of counter-weights 57, 58 mounted thereon. A connector 59 secures the said beam 53 to the said post 51, and said beam 53 is pivotally mounted on the connector 59. Stands with balance beam bag supports of the kind described are commonly used in blood banks.

FIG. 2 shows the signal apparatus 1 with the balance beam 53 in the position that it occupies when the blood collection bag 60 is full. As can be seen in FIG. 2, when blood in the bag 60 reaches a predetermined level, the beam 53 pivots about the connector 59 with the first arm 54 with the bag 60 attached thereto dropping, and the second arm 56 with the counter-weights 57, 58 mounted thereon rising. When the second arm rises, a counter-weight 58 on the second arm 56 strikes a bell 30, giving a audible signal that alerts the person in charge of drawing blood that the bag is full.

As shown in FIGS. 3, 4, and 5 the signal apparatus 1 of the present invention comprises a post-mountable arm 10 that is adapted at one end 16 for the installation of a bell 30 and that is provided with a hook 40 adapted to receive a spare bag 60 removably hung thereon.

In the preferred embodiment illustrated herein the arm 10 comprises a rectangular member 11 having a first hole 12 therethrough near a first end 13 of the said arm 10. The size and shape of the first hole 12 are determined so that a stand post 51 may be inserted through the first hole 12, and in the illustrated embodiment the first hole 12 is round and is very slightly larger in diameter than the diameter of a commonly used stand post 51. The arm 10 may be mounted onto a stand post 51 by merely inserting an end 52 of the post 51 into the first hole 12 and sliding the arm 10 along the post 51 to the desired position on the post 51. The arm 10 may be securely fastened to the post 51 to prevent further movement of the arm 10 relative to the post 51 by tightening a setscrew 14 that may be operated through a threaded second hole 15 at the first end 13 of the arm 10.

The opposite or second end 16 of the arm 10 is adapted to receive a bell 30 removably attached thereto. In the illustrated embodiment, the thickness of the arm 10 is reduced at the second end 16 of the arm 10 to accommodate the installation of a bell 30 that is commonly available. A third hole 17 is provided through the second end 16 of the arm 10. The size and location of the third hole 17 are determined so that the third hole 17 may be aligned with holes 31, 32 in a clamp that is commonly provided on the back 33 of commercially available bells 30. Also, provided is a means 34 for fastening the bell 30 to the arm 10, which means comprises a suitably sized bolt 35, washer 36 and nut 37.

What I claim is:

1. A signal apparatus comprising a vertical stand post having pivotally mounted thereon by suitable pivot connection means a balance beam having a first arm having a free end that is adapted to received a blood collection bag removably hung therefrom and a second arm having a counter-weight attached thereto a support arm having first and second ends, wherein the first end is adapted to be removably mounted on the stand post and wherein the second end is adapted to receive detachably coupled thereto a contact actuated audible signal device comprising a bell, the support arm having extending therefrom a hook adapted to receive a second bag removably hung thereon; the support arm comprising a rectangular member having a first hole therethrough near the first and thereof, said hole being adapted to receive the stand post inserted therethrough and connection means comprising a setscrew adapted to secure the support arm to the stand post and wherein the second end of the support arm is adapted to receive a bell removably attached thereto; a bell detachably coupled to the second end of the support arm; connection means for detachably connecting the bell to the support arm; wherein the counter-weight is adapted to rotate upward about the pivot connection means when blood in a blood collection bag hung from the first arm of the balance beam reaches a pre-determined level and the bell is adapted to receive a blow from the counter-weight when the counter-weight rotates upward.

* * * * *